United States Patent
Esmonde

(10) Patent No.: US 10,617,566 B2
(45) Date of Patent: Apr. 14, 2020

(54) MODULAR HEADSET FOR DIAGNOSIS AND TREATMENT OF VESTIBULAR DISORDERS

(71) Applicant: Patrick Jeremiah Esmonde, Broomall, PA (US)

(72) Inventor: Patrick Jeremiah Esmonde, Broomall, PA (US)

(73) Assignee: Vestibular First, LLC, Broomall, PA (US)

(*) Notice: Subject to any disclaimer, the term of this patent is extended or adjusted under 35 U.S.C. 154(b) by 49 days.

(21) Appl. No.: 16/008,911

(22) Filed: Jun. 14, 2018

(65) Prior Publication Data

US 2019/0380875 A1 Dec. 19, 2019

(51) Int. Cl.
| | |
|---|---|
| *A61F 9/02* | (2006.01) |
| *A61B 3/00* | (2006.01) |
| *A61B 3/113* | (2006.01) |
| *A61B 3/15* | (2006.01) |
| *A61B 3/103* | (2006.01) |
| *A61F 9/00* | (2006.01) |

(52) U.S. Cl.
CPC ............ *A61F 9/022* (2013.01); *A61B 3/0008* (2013.01); *A61B 3/103* (2013.01); *A61B 3/113* (2013.01); *A61B 3/152* (2013.01); *A61F 9/025* (2013.01); *A61F 9/029* (2013.01); *A61F 2009/0043* (2013.01)

(58) Field of Classification Search
CPC .......... A61F 9/022; A61F 9/025; A61F 9/029; A61F 2009/0043; A61B 3/0008; A61B 3/113; A61B 3/103; A61B 3/152
USPC ........................................ 351/200, 205, 206
See application file for complete search history.

(56) References Cited

U.S. PATENT DOCUMENTS

| | | | |
|---|---|---|---|
| 4,702,575 A | 10/1987 | Breglia | |
| 4,815,839 A | 3/1989 | Waldorf | |
| 4,838,681 A | 6/1989 | Pavlidis | |
| 4,988,183 A | 1/1991 | Kasahara et al. | |
| 5,093,567 A | 3/1992 | Staveley | |
| 5,822,033 A | 10/1998 | Ishikawa et al. | |
| 7,866,818 B2 | 1/2011 | Schroeder et al. | |
| 8,500,282 B2 | 8/2013 | Bolger et al. | |
| 9,332,901 B2 | 5/2016 | Eraluoto | |
| 9,332,903 B2 | 5/2016 | Geertsen | |
| 2015/0253574 A1* | 9/2015 | Thurber | G02B 27/0172 359/630 |
| 2016/0335801 A1* | 11/2016 | Yoon | G06F 3/0481 |
| 2017/0031165 A1* | 2/2017 | Costa | G02B 27/028 |
| 2018/0011329 A1* | 1/2018 | Choi | G02B 27/2257 |

OTHER PUBLICATIONS

PCT/ISA/210, dated Aug. 29, 2019 in regard to PCT/US2019/036762.
PCT/ISA/237, dated Aug. 29, 2019 in regard to PCT/US2019/036762.

* cited by examiner

*Primary Examiner* — Tuyen Tra
(74) *Attorney, Agent, or Firm* — Carl A. Ronald, Esq.

(57) ABSTRACT

In an infrared camera configuration, a modular goggle assembly can diagnose patients having vestibular dysfunction, concussion, or other maladies observable with an examination of the eyes. In a virtual reality display configuration, the assembly can be used to provide treatment to patients once the cause of the illness or malady is determined. The assembly is lightproof, mobile, and easily configurable.

2 Claims, 11 Drawing Sheets

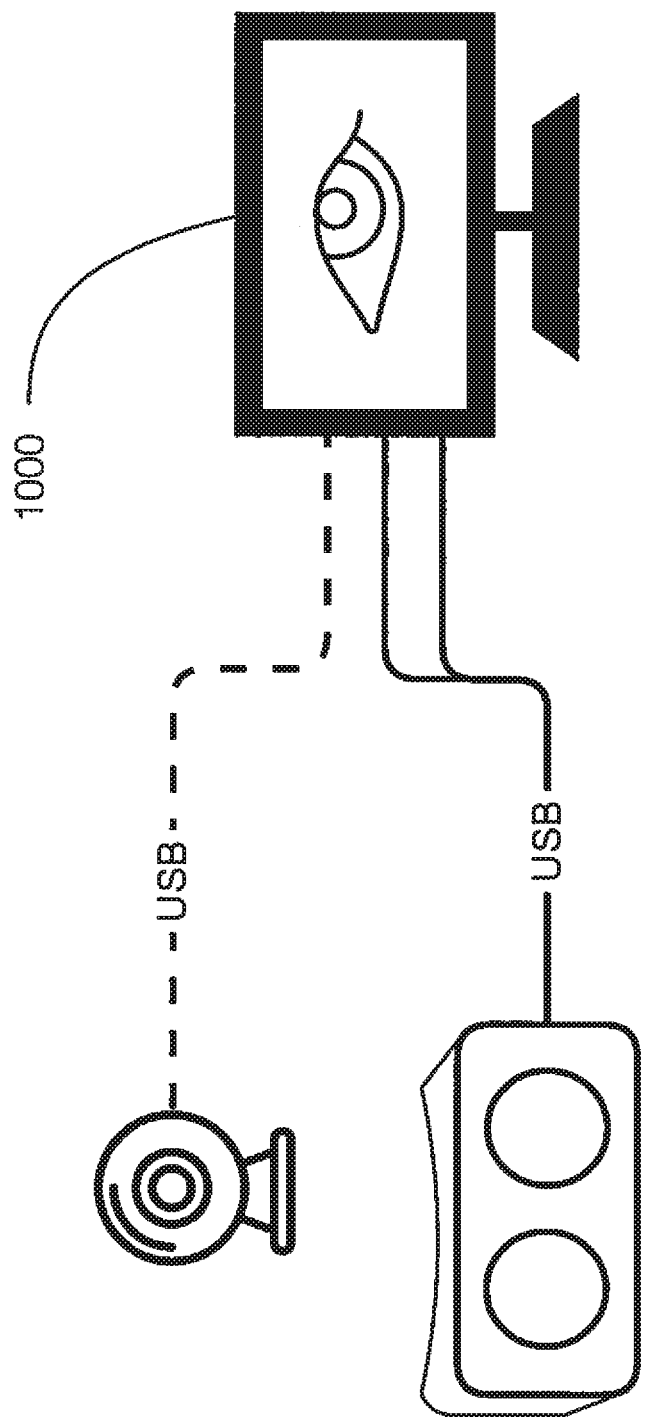

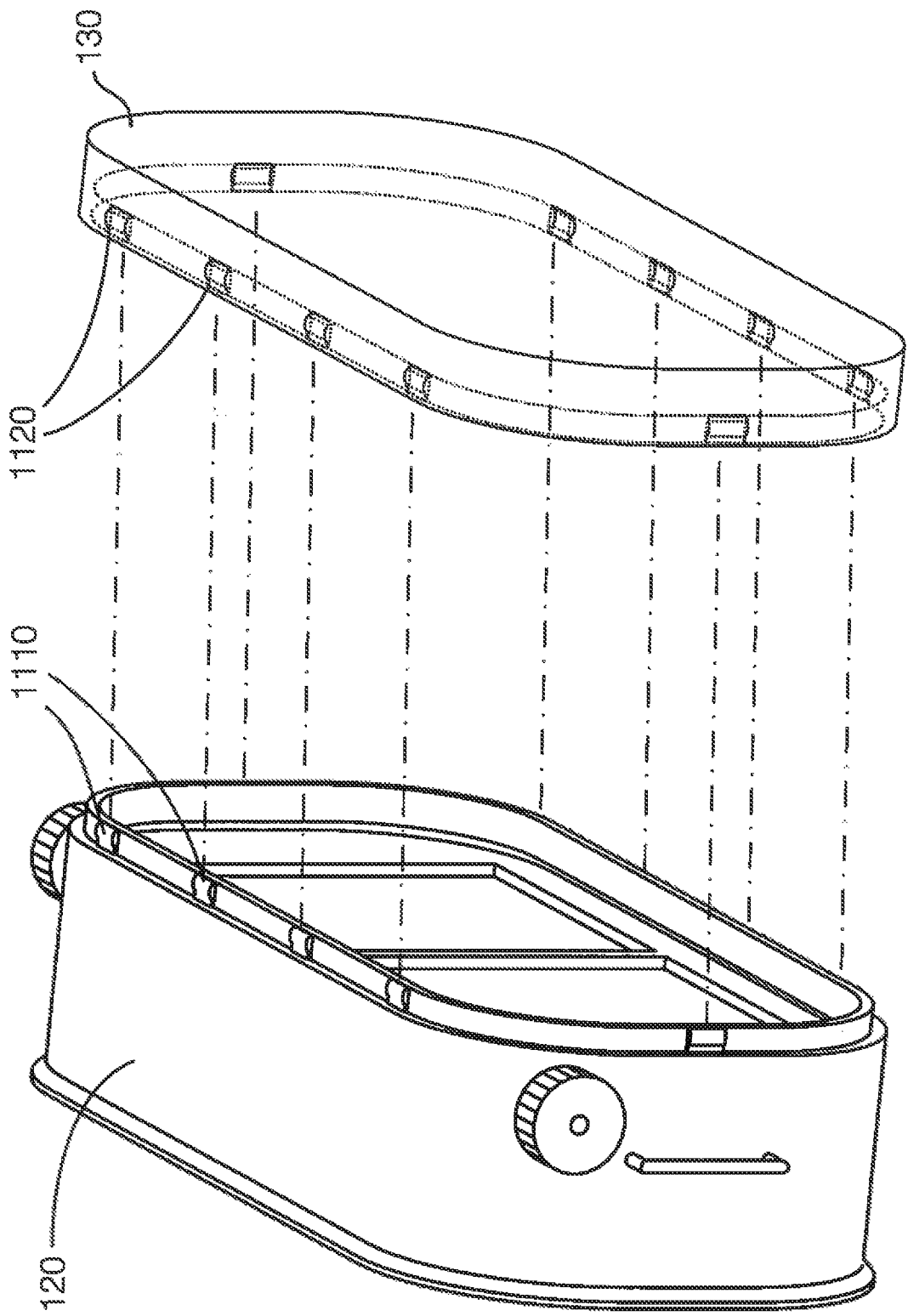

MODULAR HEADSET FOR DIAGNOSIS AND TREATMENT OF VESTIBULAR DISORDERS

FIELD OF INVENTION

The present disclosure relates to a modular goggle system and assembly that can be used not only in the assessment of certain conditions, but also in the provision of therapy to alleviate those conditions. More specifically, the present disclosure is directed to a mobile medical-grade system and assembly that can be used to help diagnose and treat vestibular dysfunction, brain disorders such as concussion or stroke, and other disorders detectable through examination of the eyes.

BACKGROUND OF THE INVENTION

Dizziness and vertigo are common symptoms reported to physicians. Technically, dizziness is defined as a feeling of lightheadedness whereas vertigo also includes the feeling of spinning. Because there are a number of different causes of dizziness or vertigo, such as visual deficits, neurological disorders, and cardiovascular disorders, among others, it can be difficult to diagnose the cause of the symptoms, which can lead to frustration and ineffective treatments being applied.

When frequent episodes of dizziness or vertigo are linked to changes in head position, however, a vestibular disorder may be suspected. Peripheral vestibular disorders are essentially a dysfunction of the balance organs of the inner ear. Central vestibular disorders, on the other hand, are disorders of the portions of central nervous system that assist with balance and spatial information.

The human body maintains balance using sensory input from the eyes, sense of touch in feet, torso, and spine, and the vestibular system in the inner ear. When there are mixed signals from these different sensory systems, the body can usually compensate. When there is a vestibular disorder, however, the body can no longer adapt and dizziness or vertigo result. Some causes of vestibular disorders include acoustic neuromas, autoimmune inner ear diseases, loose debris collecting in the inner ear sensor, head injury, degeneration of inner ear cells secondary to aging, an abnormal skin growth behind the eardrum or bone growth in the middle ear, viral inflammations of the inner ear, Meniere's disease, migraines, exposure to certain drugs or chemicals and vascular compression of the vestibular nerve, among other things.

The vestibular system is interconnected with the visual system in the human body. When the head is moved, signals are sent via the nervous system to the eye muscles so that good balance can be maintained and so that objects can stay steady in your field of vision while your head moves, also known as gaze stability. This feedback loop is known as the vestibulo-ocular reflex ("VOR"). Many tests for vestibular function leverage the VOR to identify abnormal responses when the patient's head is moved. In one such test, the patient wears specially designed goggles with cameras that focus on each eye while the eyes are in darkness inside the goggles and which are able to show the patient's eyes on a display to help determine whether a given response to the head movement is normal or indicates a problem.

In a typical diagnosis routine, a patient will put on a pair of these specially designed goggles and the clinician will have the patient look left and right and up and down with their eyes only. The clinician may also gently shake the patient's head up and down for a certain number of repetitions. Another test is to have the patient seated with his or her legs stretched out in front of them and the clinician has the patient recline with their head at a forty-five degree rotation to one side, depending on which side of the vestibular system is being tested. Based on the movements of the eyes, as shown in real-time or recorded by the cameras, the clinician is able to rule out certain disease states and possibly diagnose the source of the patient's symptoms.

Once a diagnosis has been made, a treatment regime is determined. One possible treatment involves the use of virtual reality goggles. For example, the patient will don the goggles and see either a static picture of a busy background, such as a checkerboard, or they will see a typical virtual reality moving scene such as being in a supermarket and looking around to see different products on the shelves and people walking by. The patient may be directed to view this scene for a certain amount of time or directed to interact with the environment with the goal of improving the patient's ability to tolerate more complicated and busy environments in a controlled fashion.

In order to test and treat a patient's vestibular function, specialized equipment that is either immobile or cannot easily be taken to a patient home or remote site was the only equipment available to a given clinician. What is needed is a mobile assembly or device that has interchangeable components to minimize weight and increase ease of use, transportability, and accessibility for both the clinician and the patient.

SUMMARY OF THE INVENTION

The present disclosure is directed to a modular goggle assembly that can be used in both diagnosis and treatment of vestibular disorders. In an embodiment, the modular goggle assembly comprises an ocular portion, a barrel portion and a cap portion that are connected together to create an internal chamber between the patient's eyes and a therapeutic or diagnostic device.

In embodiments, the device is a pair of infrared cameras that are mounted to a housing that can be removably placed between the barrel portion and the cap portion. The barrel portion has in internal divider so that each of the patient's eyes can be monitored by one of the cameras, whereby vestibular dysfunction can be identified.

In the configuration where infrared cameras are used, it is important that the connections between the portions be lightproof so that the diagnosis and treatment are not affected by the natural reaction of the patient's eyes, which is to fixate on or adjust to a light source. This natural reaction might interfere with patient evaluation because it could reduce or eliminate the abnormal eye movements caused by vestibular disorders. For this reason, each portion has a matingly fitted outer edge that tightly, but removably, connects to the adjacent portion. Some embodiments have a snap fit, while others use a male-female connector or even magnets to accomplish the light-proof connection.

In other embodiments, the device is an electronic device with a display capability for delivering visual stimuli to the patient's eyes for purposes of either diagnosis or treatment. The internal divider enables different stimuli to be delivered to each eye, if necessary.

In embodiments, the barrel portion has a focusing lens that can be moved closer or further from the patient to assist with focus. Further, a virtual reality configuration of the assembly includes a lens portion that provides added focusing capability for multiple patient situations.

The described assembly can also be employed as part of an overall system for diagnosing and treating vestibular disorders wherein the assembly receives a device that is communicatively connected to a large screen for ease of viewing or, in another embodiment, a computer having at least a processor and a memory wherein diagnostic processes or therapies can be presented to the clinician and, in embodiments, the results can be recorded to identify the cause of a problem or to assess the efficacy of the treatment.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings:

FIG. 10 is a schematic view of a system incorporating the modular goggle of the present invention.

FIG. 11 is an illustration of a snap-fit connection between a barrel portion and a cap portion.

DETAILED DESCRIPTION OF THE INVENTION

This disclosure is directed to example systems and assemblies for providing modular goggle assembly to assist in the diagnosis and treatment of vestibular disorders. In the following description, for purposes of explanation, numerous specific details are set forth in order to provide a thorough understanding of example embodiments. It will be evident to one skilled in the art, however, that embodiments can be practiced without these specific details. The description is not to be taken in a limiting sense, but is made merely for the purpose of illustrating the general principles of the invention, since the scope of the invention is best defined by the claims included herein.

In certain embodiments, modular goggle assemblies constructed in a manner consistent with the present disclosure use infrared cameras and, optionally, virtual reality scenes to diagnose and treat vestibular disorders in patients experiencing dizziness or vertigo. Upon diagnosis of any such disorder, a treatment plan is developed and a virtual reality configuration of the disclosed modular goggle assembly is employed to administer treatment.

Figure 1:
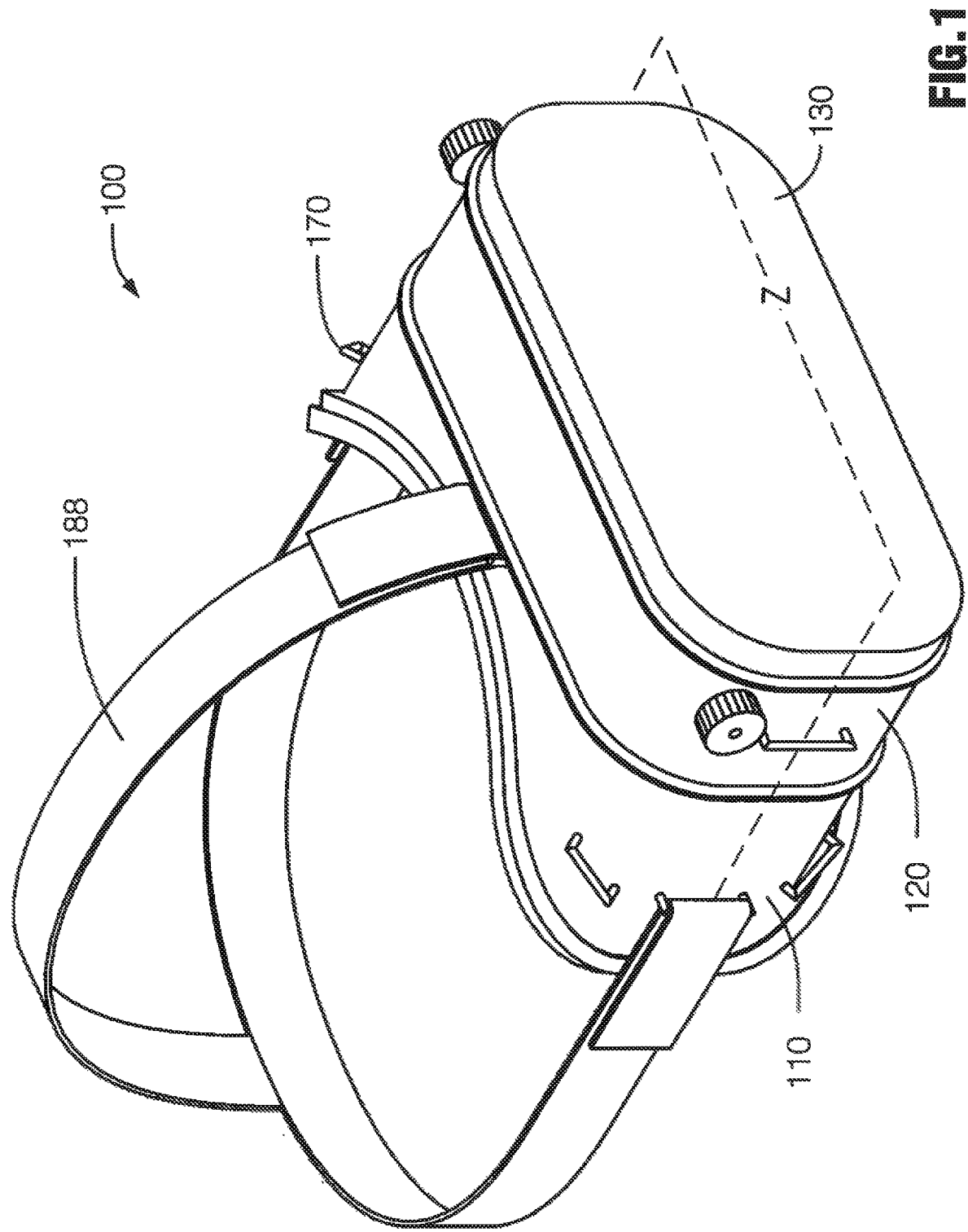
FIG. 1 is a perspective view of an infrared camera configuration of a modular goggle assembly for use in the diagnosis and treatment of vestibular dysfunction.

FIG. 1 depicts a modular goggle assembly 100 in accordance with an embodiment of the present invention. In this infrared camera configuration, the assembly 100 is comprised of an ocular portion 110, a barrel portion 120, and a cap portion 130. In embodiments, the ocular portion 110 further includes anchors 170 for connecting to a headgear 188 that permits comfortable and secure attachment of the goggle assembly 100 to the patient's head without the use of their hands.

Figure 2:
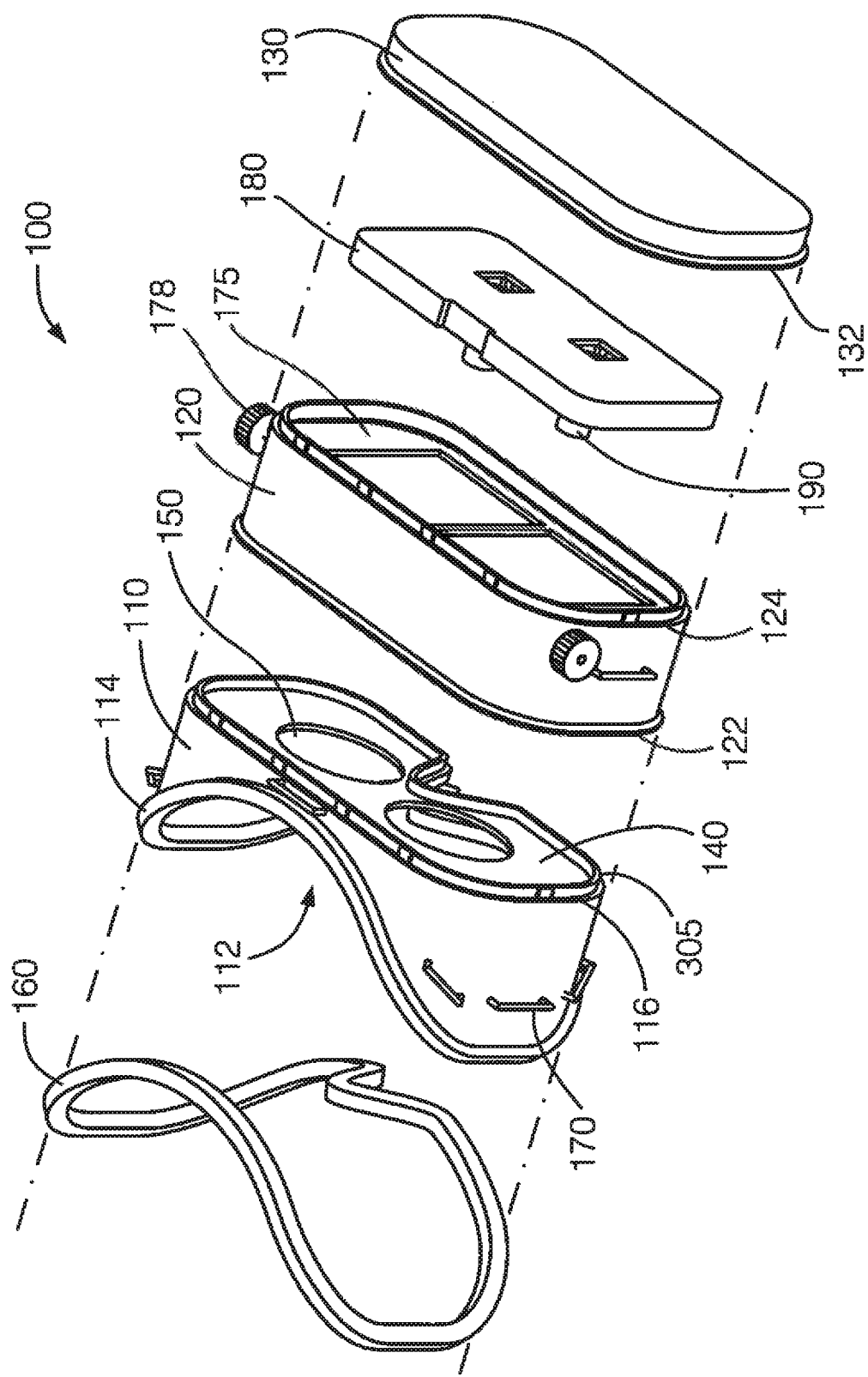
FIG. 2 is an exploded perspective view of the assembly illustrated in FIG. 1.

As illustrated by FIG. 2, the ocular portion 110 is comprised of a viewing section 140 that, in embodiments, has two apertures 150 formed therein. The ocular portion further comprises a proximal side 112 that is patient-facing and has a proximal outer rim 114 shaped to fit a patient's face. For purposes of assisting with blocking light from outside the goggle assembly 100 as well as for comfort, a cushion 160 is disposed on the proximal outer rim 114 and, in an embodiment, is removable so it can be replaced or disinfected after use. Cushion 160 is connected to the proximal outer rim 114 with hook and loop fasteners, magnets or a mechanical snap-in or other fitted, light-proof connection. In another embodiment, the materials used for the cushion are medical-grade so that they are readily cleanable and hypoallergenic.

Figure 3:
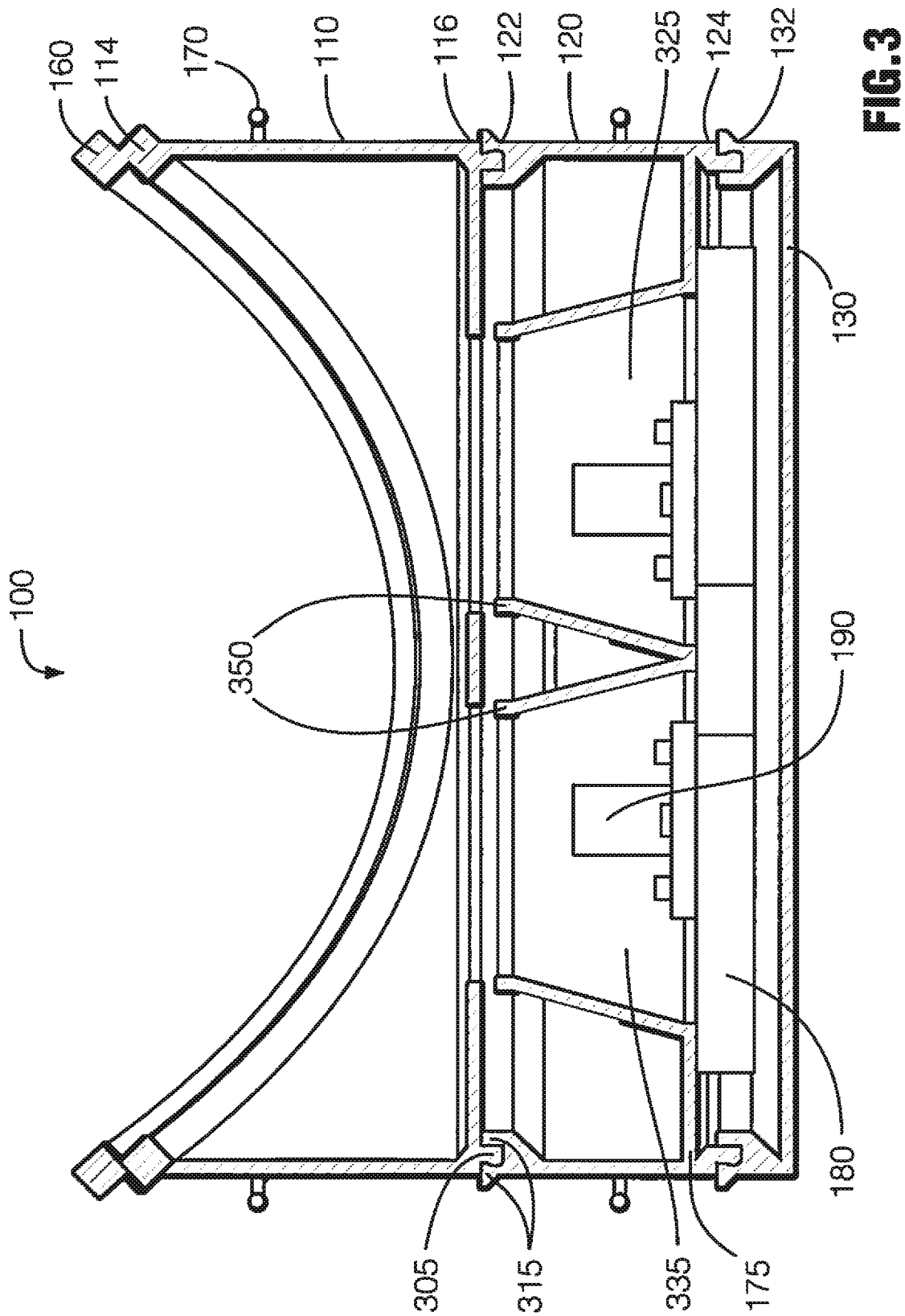
FIG. 3 is a cross-sectional plan view of the modular goggle assembly at plane Z of FIG. 1.

The distal outer rim 116 of the ocular portion 110 comprises an attachment element 305 so that it can cooperatively connect with another module or portion of the goggle assembly. As illustrated in FIG. 3, the barrel portion 120 has a mated attachment receptor 315 that receives the attachment element 305 and enables a light-proof connection between the portions. In embodiments, the connection can be a male/female fit such as a snap fit, as shown, or a tight channel fit. In other embodiments, the connection can be magnetic or even via a hook and loop fastener as is known in the art. Regardless of connection type, in an embodiment, all light is blocked from passing through the connection so that the diagnosis or therapy is uninterrupted. With continued reference to FIG. 3, an embodiment of the barrel portion has a left eye column 325 and a right eye column 335, which provides flexibility in diagnosis and treatment.

Figure 5:
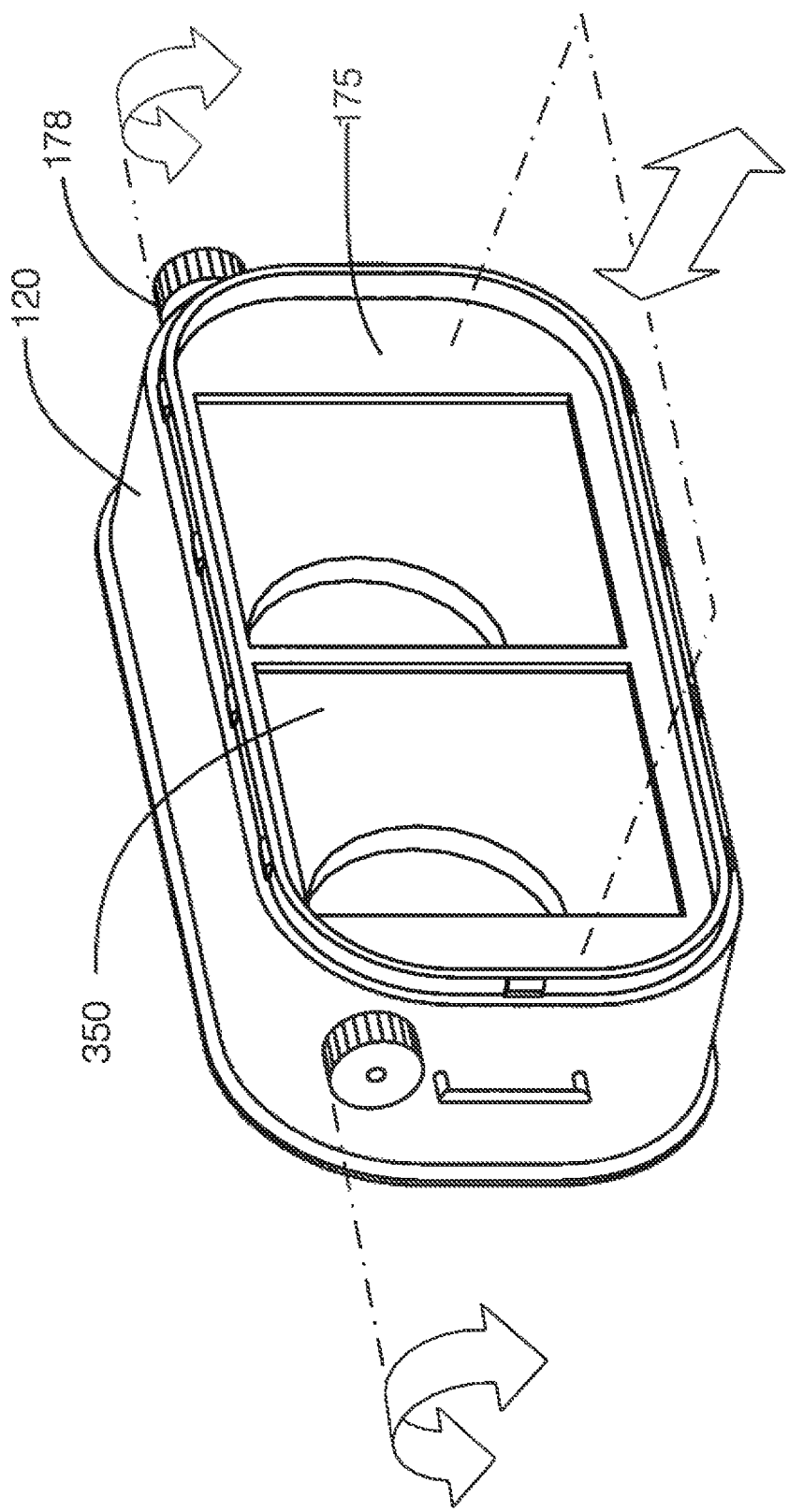
FIG. 5 is an isolated perspective view of a barrel portion consistent with an embodiment of the invention.

In the illustrated embodiment, the barrel portion 120 has a portion of the mated attachment receptor 315 situated about its proximal outer rim 122, such that the edge cooperatively and securely connects to the attachment element 305 of the distal outer rim 116 of the ocular portion 110. The barrel portion 120 also comprises an adjustable focusing plane 175 and comprises a distal outer barrel edge 124 that cooperates with the cap outer edge 132 to provide a light-proof connection with the cap portion 130. As also illustrated by FIG. 5, an adjustment dial 178 can be employed to move the adjustable focusing plane 175 closer to or further away from the ocular portion 110 in order to help with focus of the infrared cameras 190 on the eyes of the patient. In embodiments, the barrel contains a divider 350 that creates a left chamber and a right chamber to permit the cameras 190 to focus on one eye at a time and so that different content can be delivered to each eye when the assembly is in virtual reality mode.

Figure 4:
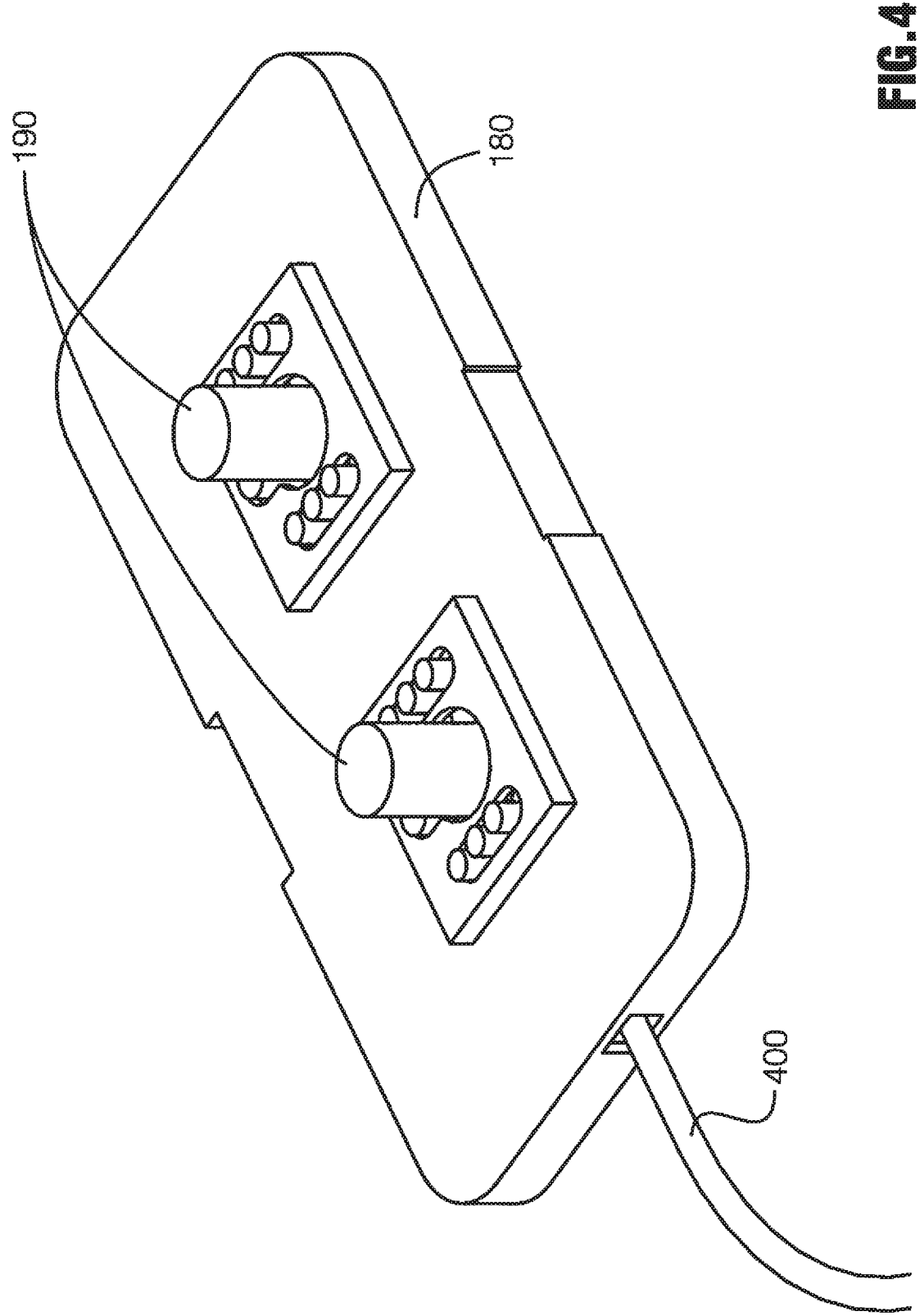
FIG. 4 is a perspective view of a camera housing holding two infrared cameras in accordance with an embodiment of the invention.

In embodiments, a camera housing 180 is removably positioned in between the barrel portion 120 and the cap portion 130 with hook and loop fasteners, magnets or a mechanical snap-in or other fitted connection. With reference to FIG. 4, the camera housing 180 supports two infrared cameras 190 that are mounted on or in the camera housing 180 so that they face the patient's eyes. In embodiments, the cameras 190 provide information about the patient's eye movements during diagnosis or therapy related to a vestibular disorder or other illness, injury, or disease. In embodiments, the cameras provide data to a computer or display 1000 as illustrated in FIG. 10. The connection to the computer or display 1000 can be wireless or wired 400. In embodiments, the wired connection 400 to the computer or display 1000 is via the USB protocol as is known in the art, but other connections and protocols will be readily apparent to those of skill in the art. The computer 1000, as is known in the art, will comprise at least a processor and a connected memory capacity for storing and running therapeutic or diagnostic routines and capturing and storing infrared camera output for analysis by a clinician.

With continued reference to FIGS. 2 and 3, the cap portion 130 has a cap outer rim 132 that, in embodiments, is formed as an attachment receptor that is designed to mate with and receive an attachment element just as previously discussed with the ocular portion 110 and barrel portion 120 connection. In embodiments, the attachment elements and receptors can be reversed so that the element is on the portion further from the patient and the receptor is on the portion closer to the patient's face. In another embodiment illustrated in FIG. 11, the cap portion 130 can be attached to the barrel portion 120 in a friction mount using the convex tabs 1110 to connect with the complementary concave indentions 1120 so that the cap portion 130 is firmly attached and the assembly 100 is lightproof.

Figure 6:
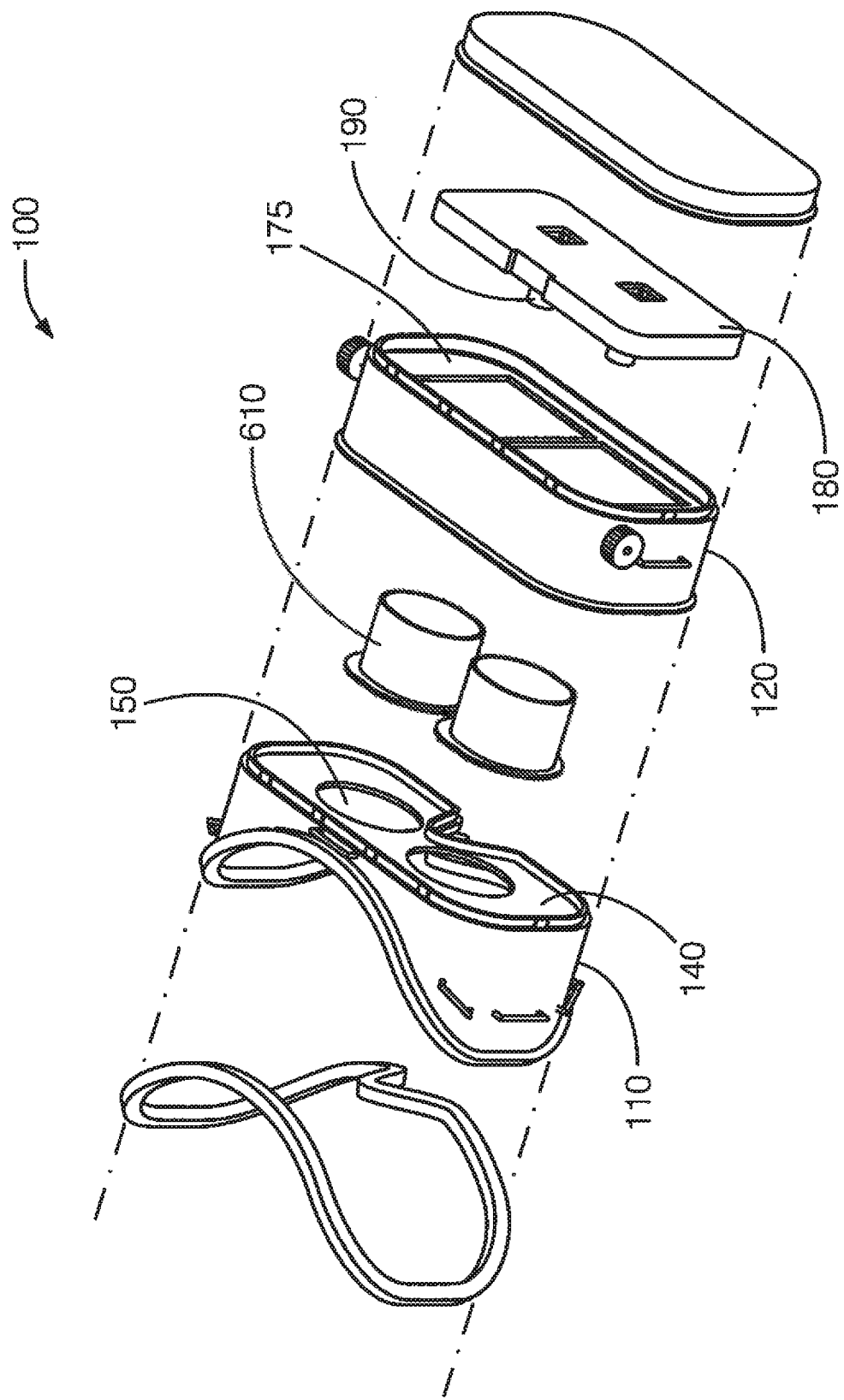
FIG. 6 is an exploded view of an alternate embodiment of the infrared camera configuration.

FIG. 6 illustrates an alternative embodiment of the modular goggle assembly 100 of the present invention. In this embodiment, an off-the-shelf Virtual Reality goggle, such as the Samsung Gear VR®, has been modified in the viewing section 140, with the addition of light-blocking columns 610 fastened to the surface of the viewing section 140 to centered with the pair of apertures 150. To ensure darkness inside the chamber between the patient's eyes and the cameras 190, a pair of light blocking columns 610 are attached to the ocular portion 110 added in this embodiment to prevent light from the barrel portion 120 from entering the field of view of the cameras 190 when moving the adjustable focusing plane 175 within the barrel. This ensures proper operation of the cameras when they are in an infrared mode. Samsung Gear VR® is a registered trademark of Samsung Electronics Co., Ltd.

Figure 7:
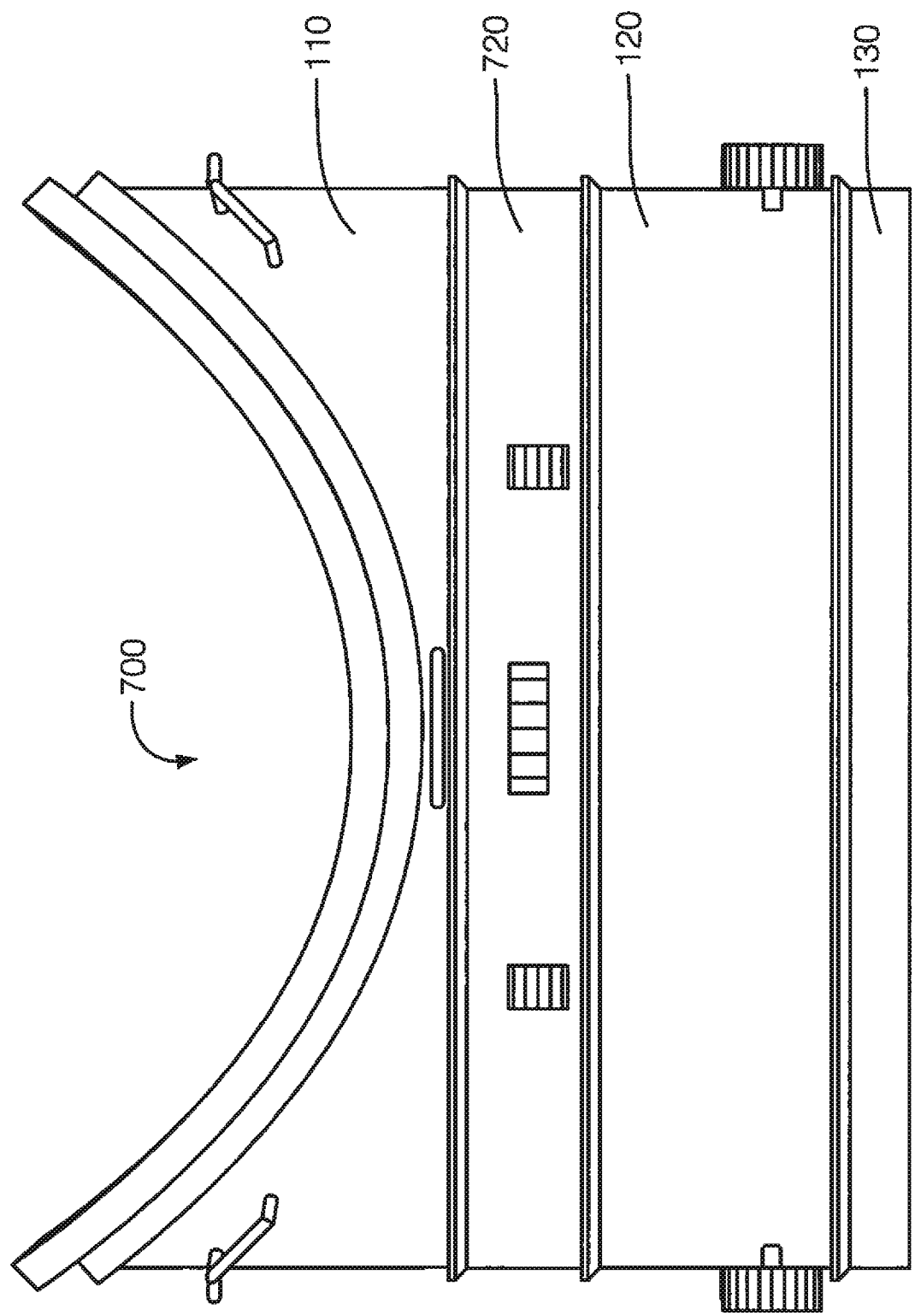
FIG. 7 is a plan view of a virtual reality configuration of a modular goggle assembly for use in the treatment of vestibular dysfunction.

FIG. 7 illustrates a plan view of a modular goggle assembly 700 in a virtual reality display configuration consistent with an embodiment of the disclosed invention. In this configuration a lens portion 720 is inserted in between the ocular portion 110 and the barrel portion 120. Again, a cap portion 130 is attached to the end of the barrel portion 120.

Figure 8:
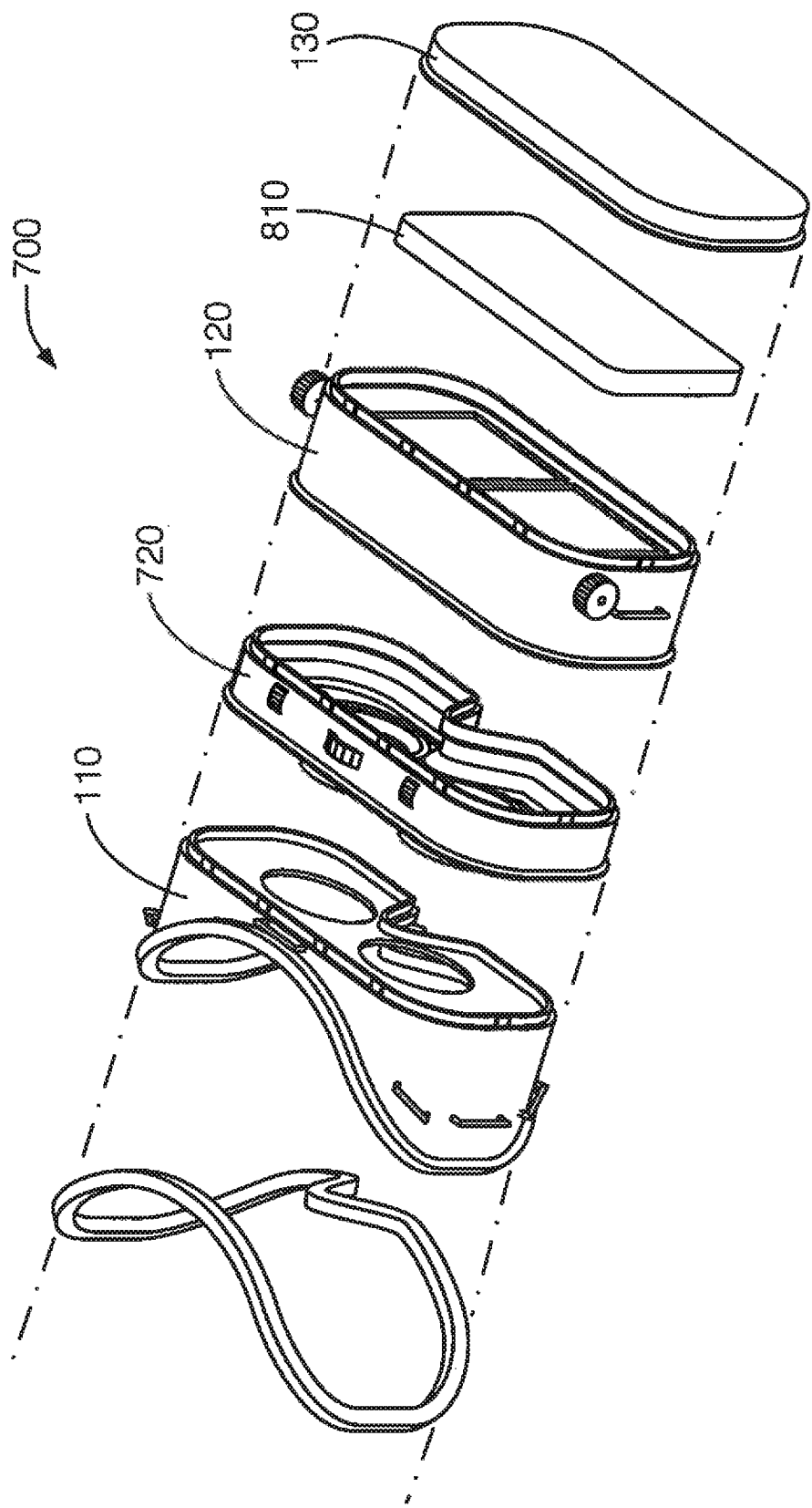
FIG. 8 is an exploded perspective view of the assembly illustrated in FIG. 7.

FIG. 8 is an exploded view of the modular goggle assembly 700 in the virtual reality display configuration. In this embodiment, there is no camera housing. Instead, there is a display device 810 such as a mobile phone or other device capable of displaying images or video as is known in the art that is inserted or otherwise attached in between the barrel portion 120 and the cap portion 130 in the same way as the IR camera housing was inserted into the infrared camera configuration. In embodiments, the display device 810 is connected either via a wired connection or wirelessly, to a computer 1000 as illustrated in FIG. 10 having at least a processor and a memory facility for storing and delivering one or more therapeutic or diagnostic programs to be displayed to the patient the course of treatment or diagnosis of a vestibular disorder.

Another difference between the infrared camera configuration and the virtual reality configuration is the addition of the lens portion 720. In an embodiment, the lens portion 720 includes lenses having different levels of magnification to optimize for specific virtual reality applications. The lens portion 720 may also include colored or filtered lenses that block or allow certain spectrums of light for a research functionality. In further embodiments, the lenses can have different shapes, such as concave, convex, or Fresnel.

Figure 9:
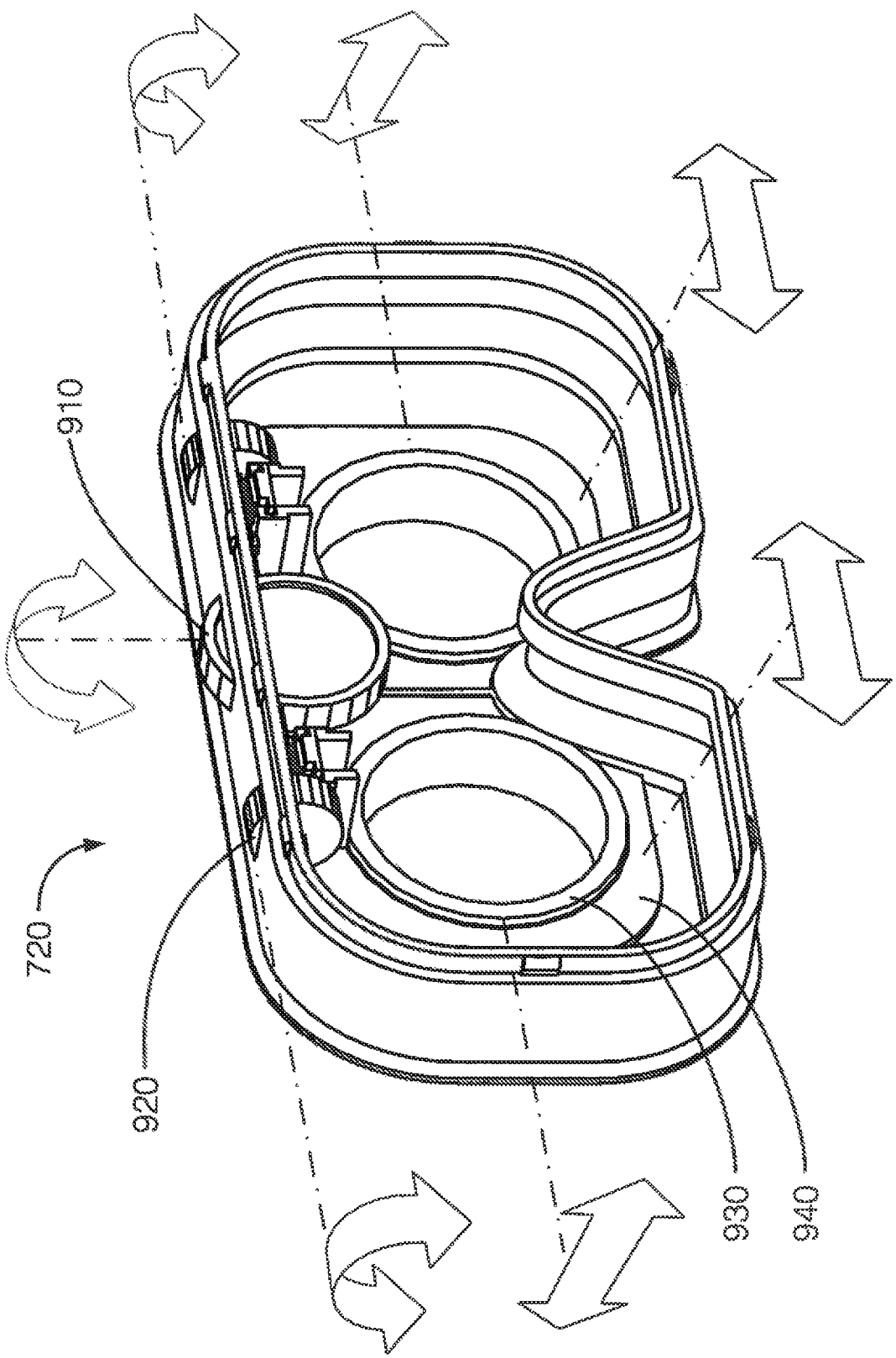
FIG. 9 is an isolated perspective view of a lens portion consistent with an embodiment of the invention.

FIG. 9 illustrates an isolated view of the lens portion 720. In addition to providing lenses of different magnifications and types, the lens portion enables the lenses to be placed at differing distances from the patient's eyes. In embodiments, the lens adjustment dial 920 is employed to move the lens barrel 930 closer or further from the patient when in use. Likewise, the width adjustment dial 910 moves the lens barrel holders 940 closer or further from each other to conform to different patients. In an embodiment, the lens adjustment dial 920 and width adjustment dial 910 are connected to a rack and pinion system to enable movement of the lens barrel holders 940 and lens barrels 930. In other embodiments, the dials 910, 920 are attached to gears that move the lens barrel holders 940 and lens barrels 930 in a manner known to those of skill in the art.

In certain embodiments, the modular goggle assembly 100 is used by a clinician who may go to a patient's house or may have several offices and may need to bring the modular goggle system with them to evaluate patients. Upon suspicion of some malady detectable through eye movements, the clinician may have the patient don the modular goggle assembly 100 in an infrared camera configuration as represented by FIG. 1. To the extent that a diagnosis is made by the clinician upon reviewing the eye movements of the patient, the clinician can quickly and optionally switch to a virtual reality display configuration, as demonstrated by FIG. 7, by removing the IR camera housing 180 from the cap portion 130 and inserting a cell phone or other properly sized display device 810 in the cap portion 130 as well as a lens portion 720 in between the ocular portion 110 and the barrel portion 120, if necessary.

It is hoped that a modular goggle assembly 100, constructed in accordance with the present disclosure, can be used by general practitioners and urgent care providers alike to quickly triage patients suffering from vertigo. Early diagnosis means faster treatment and faster treatment means an overall lower cost of healthcare.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain and which fall within the limits of the appended claims.

I claim:

1. A system for diagnosing and treating vestibular disorders of a patient comprising a modular goggle assembly having at least an ocular portion, a barrel portion and a cap portion and a diagnostic or therapeutic device, wherein the device is removably disposed into the modular goggle assembly; and wherein the system is convertible between a virtual reality display configuration wherein the device is comprised of a mobile phone or display device and an infrared camera configuration wherein the device is comprised of two infrared cameras directed at the patient's eyes.

2. The system of claim 1, wherein the infrared cameras are mounted to a housing and said housing is releasably mounted between the barrel portion and the cap portion.

* * * * *